United States Patent
Bastyr et al.

[11] Patent Number: 6,110,137
[45] Date of Patent: Aug. 29, 2000

[54] ORTHOPAEDIC BRACE HAVING ONE-PIECE CUFF

[75] Inventors: Charles A. Bastyr; Joseph F. Nebolon, both of San Diego, Calif.

[73] Assignee: DJ Orthopedics, LLC, Vista, Calif.

[21] Appl. No.: 08/770,651

[22] Filed: Dec. 19, 1996

Related U.S. Application Data

[63] Continuation of application No. 08/368,294, Jan. 3, 1995, abandoned.

[51] Int. Cl.⁷ ......................................................... A61F 5/00
[52] U.S. Cl. ..................................... 602/26; 602/5; 602/6; 602/7; 602/8
[58] Field of Search ................................ 602/5–8, 16, 20, 602/23, 26

[56] References Cited

U.S. PATENT DOCUMENTS

| | | |
|---|---|---|
| 950,143 | 2/1910 | Saxe . |
| 2,287,821 | 6/1942 | O'Donovan . |
| 3,493,456 | 2/1970 | Vilutis . |
| 3,710,790 | 1/1973 | Lemon . |
| 3,799,158 | 3/1974 | Gardner . |
| 4,084,586 | 4/1978 | Hettick . |
| 4,241,730 | 12/1980 | Helfet . |
| 4,271,831 | 6/1981 | Deibert . |
| 4,672,955 | 6/1987 | Cooper . |
| 4,697,583 | 10/1987 | Mason et al. . |
| 4,700,698 | 10/1987 | Kleylein . |
| 4,832,010 | 5/1989 | Lerman . |
| 4,850,341 | 7/1989 | Fabry et al. . |
| 4,938,206 | 7/1990 | Harris et al. .............................. 602/16 |
| 4,955,369 | 9/1990 | Bledsoe et al. . |
| 4,961,418 | 10/1990 | McLaurin-Smith . |
| 5,009,223 | 4/1991 | DeFonce ............................... 602/26 X |
| 5,022,391 | 6/1991 | Weidenburner ........................ 602/26 X |
| 5,042,464 | 8/1991 | Skwor et al. .......................... 602/26 X |
| 5,058,573 | 10/1991 | Hess et al. . |
| 5,063,916 | 11/1991 | Frarce et al. .............................. 602/26 |
| 5,078,127 | 1/1992 | Daneman et al. . |
| 5,092,318 | 3/1992 | More et al. . |
| 5,092,320 | 3/1992 | Maurer . |
| 5,105,805 | 4/1992 | Lapointe et al. ....................... 602/26 X |
| 5,185,000 | 2/1993 | Brandt et al. . |
| 5,217,431 | 6/1993 | Toronto et al. . |
| 5,286,249 | 2/1994 | Thibodaux . |
| 5,288,287 | 2/1994 | Castillo et al. ........................ 602/26 X |
| 5,292,303 | 3/1994 | Bastyr et al. . |

(List continued on next page.)

FOREIGN PATENT DOCUMENTS 0486241  5/1992  European Pat. Off. .

OTHER PUBLICATIONS

Selected Pages From Smith & Nephew Donjoy Inc. Sales Support Manual, "Golfpoint by Donjoy," Aug. 1993.
Selected Pages From Smith & Nephew Donjoy Inc. Sales Support Manual, "Combined Instability Knee Brace," Mar. 1993.
Selected Pages From Smith & Nephew Donjoy Inc. Sales Support Manual, "Defiance," Jul. 1992.

*Primary Examiner*—Jerome W. Donnelly
*Assistant Examiner*—Jayne Saydah
*Attorney, Agent, or Firm*—Knobbe, Martens, Olson and Bear, LLP

[57] ABSTRACT

An orthopaedic brace having a cuff formed as a single piece from bendable sheet material comprises a generally U-shaped frame having a center segment and two extensions projecting from the ends of the center segment in a common direction. The center segment has a reduced stiffness as compared to the extensions to permit the center segment to be more readily shaped to conform to the body part of a wearer. A molded one-piece covering, such as a thermoplastic material, forms a continuous covering surrounding portions of the cuff. The cuff may be fabricated by stamping it from a sheet of metal, such as aluminum, or a composite material. By forming the sheet such that it has a variable thickness along one edge thereof, the center segment may be formed by the portion of the sheet having reduced thickness, while the extensions may be formed from the remainder of the sheet.

17 Claims, 3 Drawing Sheets

U.S. PATENT DOCUMENTS

| | | |
|---|---|---|
| 5,306,229 | 4/1994 | Brandt et al. . |
| 5,316,547 | 5/1994 | Gildersleeve . |
| 5,330,419 | 7/1994 | Toronto et al. . |
| 5,360,394 | 11/1994 | Christensen ............................ 602/26 |
| 5,383,844 | 1/1995 | Munoz et al. . |
| 5,383,845 | 1/1995 | Nebolon . |
| 5,385,534 | 1/1995 | Cassford . |
| 5,409,449 | 4/1995 | Nebolon . |
| 5,415,625 | 5/1995 | Cassford et al. . |
| 5,458,565 | 10/1995 | Tillinghast, III et al. ................ 602/26 |
| 5,527,267 | 6/1996 | Billotti . |
| 5,527,268 | 6/1996 | Gildersleeve et al. .................... 602/26 |
| 5,554,104 | 9/1996 | Grim .................................... 602/26 X |

ORTHOPAEDIC BRACE HAVING ONE-PIECE CUFF

This is a Continuation of application Ser. No. 08/368,294, filed Jan. 3, 1995, abandoned.

BACKGROUND OF THE INVENTION

The present invention relates to orthopaedic braces and, more particularly, to an orthopaedic brace having a cuff formed as a single piece from bendable sheet material.

When a joint has been weakened by injury or other infirmity, orthopaedic braces often are used to stabilize and protect the joint during the rehabilitation process. A typical brace comprises a number of rigid structural components dynamically linked together by hinges, such that the axes of the hinges align with the joint being stabilized. The rigid structural components are secured to the body of the wearer above and below the joint by flexible straps to support and protect the joint when the wearer is active.

By way of example, when the knee is injured, a knee brace can be used to stabilize the knee joint which connects the upper leg (i.e., the femur) and the lower leg (i.e., the tibia). Typical knee braces comprise an upper leg cuff that generally conforms to the shape of the upper leg above the knee joint and a lower leg cuff which generally conforms to the shape of the lower leg below the knee joint. The upper and lower leg cuffs are dynamically connected to each other by hinges in alignment with the knee joint.

The upper and lower leg cuffs of the knee brace usually are of a three-piece construction, comprising a center band which conforms to the leg of the wearer, and two elongated bars connected to the ends of the center band. The bars extend away from the center band in a common direction toward the knee joint, where they terminate in a toothed configuration forming a part of the hinge. The cuffs generally are constructed from metal which preferably is coated with a rubber-like covering. The rubber-like covering is designed to protect the wearer and others from exposed metal parts on the brace which could cause injury, for example, during an athletic event.

Problems have existed in the past regarding orthopaedic braces, such as knee braces having a three-piece construction of the type described above. For example, the ends of the bars are usually joined to the ends of the center band by rivets inserted through aligned holes in the overlapping portions of the center band and bars. Since the bars and center band are each coated with a rubber-like material prior to assembly in overlapping relation by the rivets, the rubber-like coating adds to the overall thickness of the cuff in the area where the center band is riveted to the bars. Because the connection between the bars and center band is not a metal-to-metal connection, the cuff is susceptible to being weakened, and sometimes loosened, in the area of the riveted connection.

Another drawback of the three-piece orthopaedic brace is attributable to the labor costs that are associated with the multiple manufacturing steps that must be taken to assemble each cuff. First, the center band and bars must be fabricated and thereafter separately coated with the rubber-like covering. After the rubber-like covering has been applied, the ends of the bars are connected to the center band by the rivets, followed by bending of the center band to conform to the leg of the wearer. All of these separate fabrication and assembly steps add to the overall cost of the brace.

Further, the construction of orthopaedic braces having cuffs of this type are not conducive to a lightweight brace. It also is difficult to produce an orthopaedic brace having a streamlined appearance, due to the rivets and bulk produced from the overlapping components.

Accordingly, there has existed a definite need for an orthopaedic brace cuff which eliminates the use of rivets, which is more streamlined in appearance, which can be constructed using a reduced amount of labor without sacrificing structural integrity, and which is as lightweight as possible. The present invention satisfies these and other needs, and provides further related advantages.

SUMMARY OF THE INVENTION

The present invention is embodied in an orthopaedic brace for use in stabilizing a joint that, for example, has been weakened by injury or other infirmity. The brace comprises a cuff formed of a single piece that is shaped to conform to the body part of a wearer. A molded one-piece covering is applied to selected portions of the cuff so that no metal parts are exposed. This one-piece construction provides an orthopaedic brace cuff that is streamlined in appearance, relatively inexpensive to manufacture, light in weight, yet provides an extremely strong brace.

More particularly, the cuff of the orthopaedic brace comprises a general U-shaped frame formed as a single piece from bendable sheet material. With reference to an embodiment of the invention in which the brace comprises a knee brace, for example, the frame has a center segment which is bent in an arcuate manner to conform to the leg of the wearer, and two extensions projecting from the ends of the center segment. These extensions project from the center segment in a common direction toward the knee joint where they terminate in a toothed configuration to form part of a hinge. The knee brace preferably comprises an upper leg cuff and a lower leg cuff joined to each other by hinges on opposite lateral sides of the knee joint.

In one aspect of the invention, the center segment of the cuff has a reduced stiffness as compared to the stiffness of the extensions. This allows the center segment to more easily bend during the manufacturing process and conform to a particular shape. However, the stiffness in the extensions is not reduced, thereby providing the necessary structural strength in this area of the brace. In one embodiment, the reduced stiffness of the center segment is provided by forming the center segment from a material having a reduced thickness as compared to the thickness of the extensions. Preferred materials for forming the cuff include metal, such as aluminum, or a composite material.

In another aspect of the invention, a series of apertures are provided in the center segment. These apertures are designed to render the center segment lighter and more readily bendable during the fabrication process.

In still another aspect of the invention, all or selected portions of the cuff are coated with a molded one-piece covering that closely and securely engages opposite surfaces of the cuff. In the preferred embodiment, the covering comprises a thermoplastic material, such as Krayton or other suitable rubber-like materials. If desired, the covering can be applied to the center segment so as to define a recess for receiving a pad or cushion designed to contact the wearer's leg. The portion of the covering defining the perimeter of the cuff around the recess may further define a raised lip. This raised lip assists in aligning the pad to the center segment.

The cuff preferably is fabricated from sheet material, for example, an elongated flat sheet of metal, such as aluminum, or a composite material. The sheet has a longitudinal portion along one edge having a thickness that is reduced as compared to the thickness of the remainder of the sheet. Using stamping techniques, a plurality of the U-shaped frames forming the cuff can be stamped from the sheet. Each frame that is stamped, therefore, will comprise a single-piece construction, having the center segment and two extensions projecting from the ends of the center segment in a common direction, as described above. However, the center segment of the frame is formed by the portion of the sheet that is of reduced thickness, and the extensions are formed from the remainder of the sheet which is thicker. This advantageously yields a frame that is more easily bendable at the center segment during the fabrication process, yet provides a high degree of structural strength in the extensions.

The sheet material may be fabricated by an extrusion process which forms the longitudinal portion of the sheet with the reduced thickness. Alternatively, the sheet may be machined along the longitudinal portion to reduce its thickness.

After the frame has been produced by the stamping process described above, the frame is placed in a cavity of a mold where the covering is applied. Once in the cavity, thermoplastic material or other suitable rubber-like covering material, heated and in liquid form, is introduced into the mold and allowed to harden. Once hardened, a rubber-like covering is formed on the frame that covers at least a portion of opposite surfaces of the center segment and the extensions to prevent injury that could result from exposed metal surfaces. After the frame is removed from the mold, the center segment is bent in a generally arcuate shape to conform to the leg of the wearer. It will be appreciated that the cuffs can be mass produced in a variety of sizes, and the center segments can be bent into a variety of arcuate shapes, to produce a plurality of cuffs for forming knee braces and other types of orthopaedic braces in a variety of different sizes and configurations.

By forming the cuff as a single piece and then coating it with the rubber-like covering, a very strong, lightweight cuff is produced in fewer manufacturing steps at a relatively low cost. Increased strength is provided because there are no overlapping joints connected by rivets or other fasteners that could tend to weaken or otherwise loosen during use. Since there are no overlapping joints where the extensions are joined to the center segment, the cuff can be shaped so as to have a more streamlined and desirable cosmetic appearance. The reduced thickness in the area of the center segment, together with the apertures, reduces the weight of the cuff and thereby provides an overall knee brace that is as lightweight as possible.

Other features and advantages of the present invention will become apparent from the following detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DESCRIPTION OF THE PREFERRED EMBODIMENT

Figure 1:
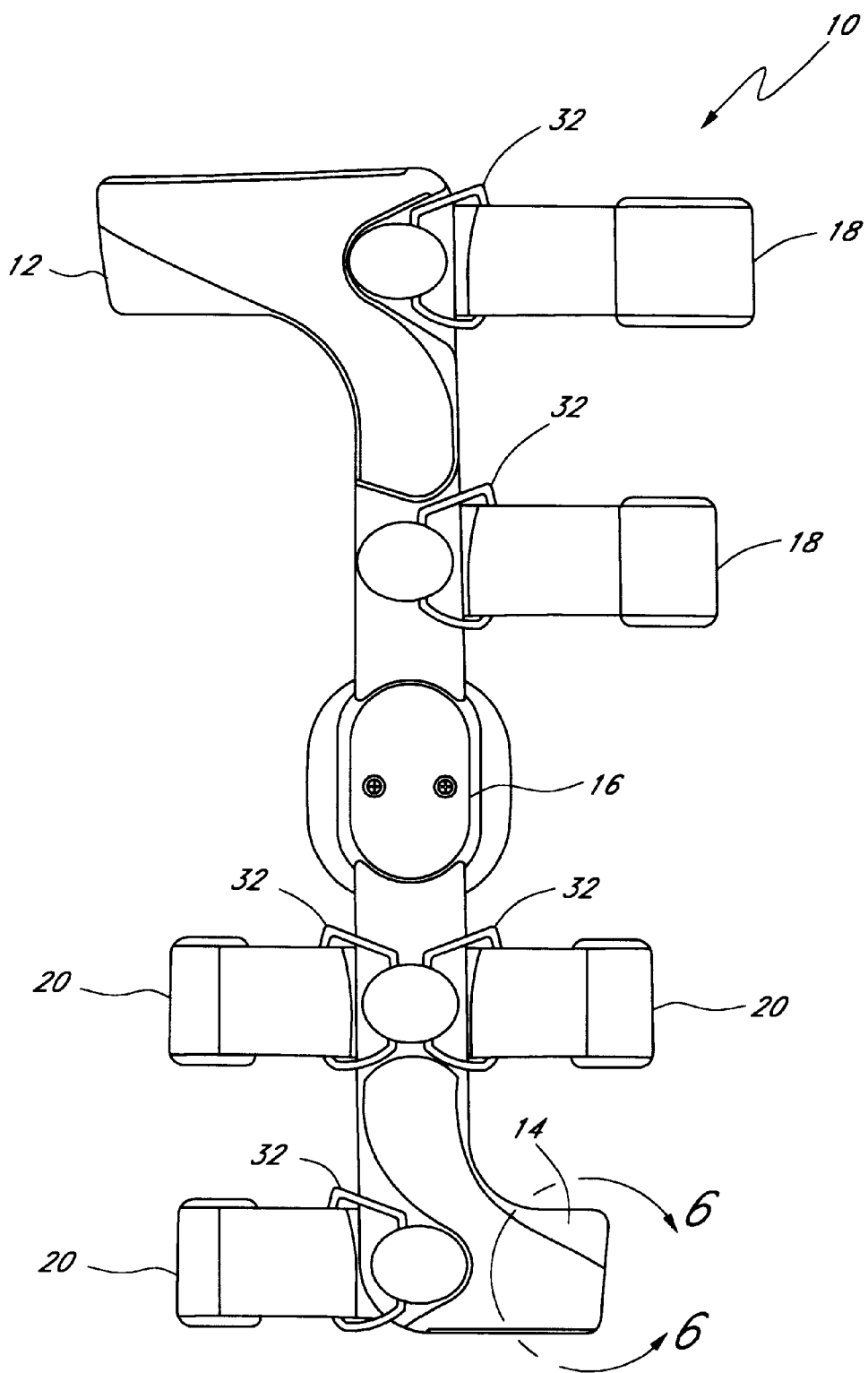
FIG. 1 is a side elevational view of a knee brace embodying the novel features of the present invention.

As shown in the exemplary drawings, the present invention is embodied in an orthopaedic brace, generally referred to by the reference numeral 10, for use in supporting and stabilizing a joint. The orthopaedic brace 10 shown in the drawings comprises a knee brace having an upper leg cuff 12 and a lower leg cuff 14 that are dynamically connected together by hinges 16 on opposite lateral sides of the knee joint. (See FIG. 1). A pair of adjustable upper leg straps 18 and lower leg straps 20 are provided to secure the knee brace 10 to the wearer's leg. It will be appreciated, however, that the invention can be embodied in orthopaedic braces other than knee braces. Therefore, the knee brace 10 shown in the drawings should be considered as being exemplary.

Figure 2:
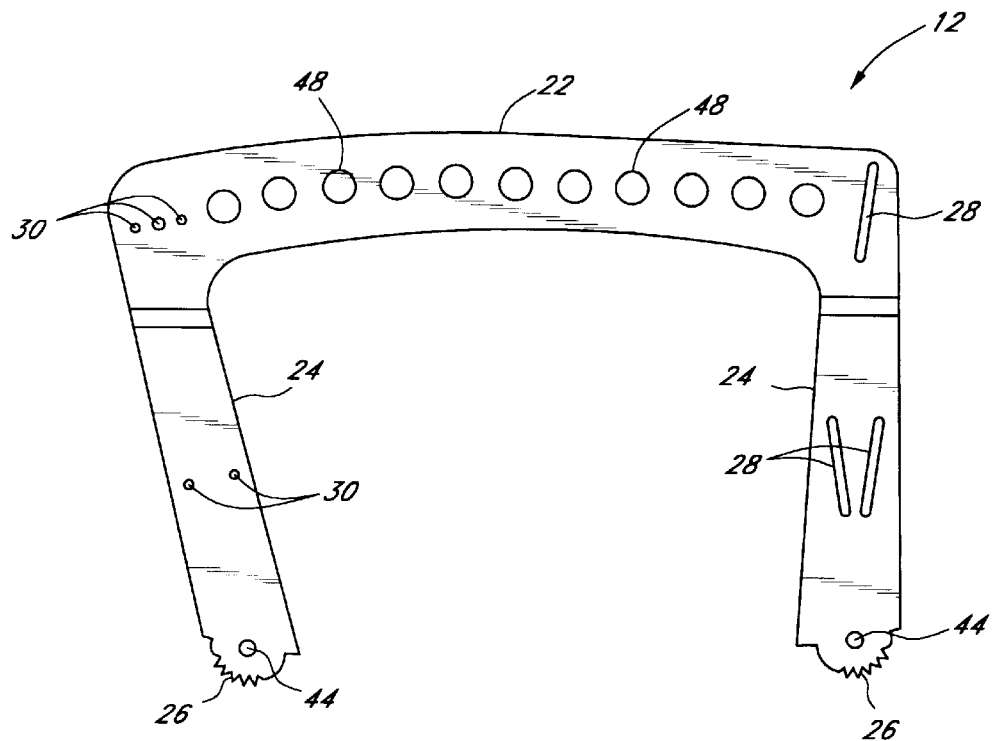
FIG. 2 shows a cuff of the knee brace, prior to being bent to conform to the upper leg of a wearer.
Figure 3:
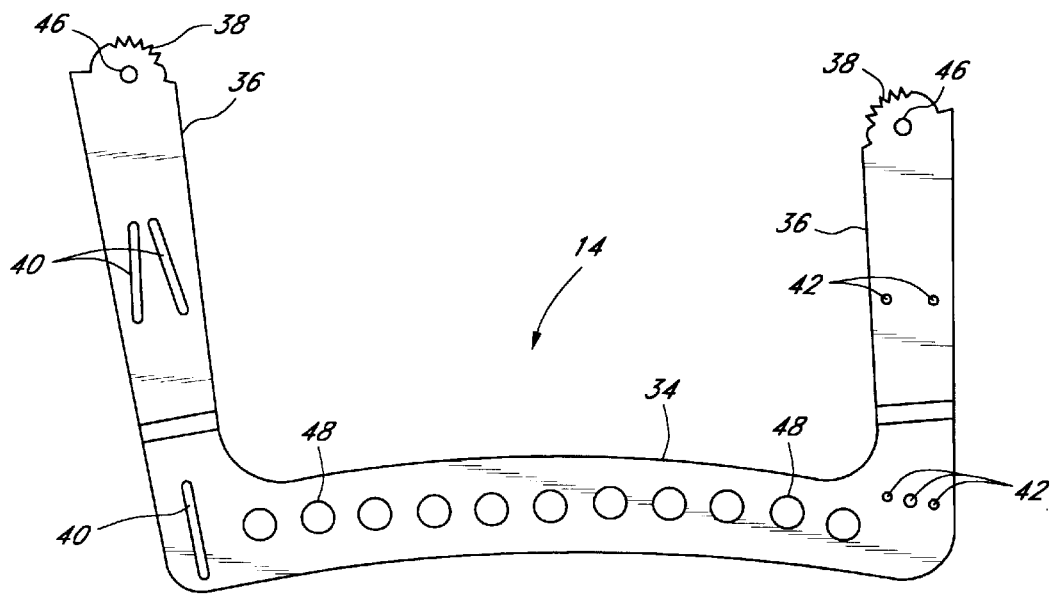
FIG. 3 shows another cuff of the knee brace, prior to being bent to conform to the lower leg of the wearer.

In accordance with the invention, the upper and lower leg cuffs 12 and 14 each comprise a one-piece frame formed from bendable sheet material. FIG. 2 shows the upper leg cuff 12, and FIG. 3 shows the lower leg cuff 14, both of which have a substantially U-shaped configuration prior to being bent to conform to the shape of a wearer's leg. With reference to FIG. 2, the upper leg cuff 12 comprises a center segment 22 and a pair of extensions 24 extending away from the ends of the center segment in a common direction. Since the upper leg cuff 12 comprises a one-piece construction, the ends of the extensions 24 joined to the center segment 22 are integrally formed with it. The opposite ends of the extensions 24 that extend away from the center segment 22 terminate in a toothed configuration comprising a plurality of teeth 26.

The upper leg cuff 12 also includes a plurality of slots 28 and holes 30. The holes 30 along one extension 24, and also at the end of the center segment 22, are provided to enable adjustment of the upper leg straps 18 with respect to the cuff 12 using clips 32 during attachment or repositioning of the brace 10 on the wearer's leg. (See FIG. 1). Similarly, the slots 28 along the opposite extension 24, and also at the other end of the center segment 22, slidably receive the ends of the upper leg straps 18 to enable mounting of the straps to the brace 10.

The lower leg cuff 14 shown in FIG. 3 similarly comprises a center segment 34 and two extensions 36 integrally connected to the ends of the center segment. The extensions 36 project away from the center segment 34 in a common direction and terminate in a plurality of teeth 38. The teeth 38 on the lower leg cuff 14, in cooperation with the teeth 26 formed on the upper leg cuff 12, mesh with each other to form part of the hinges 16 on opposite lateral sides of the knee joint. These hinges 16 allow the upper leg cuff 12 and the lower leg cuff 14 to pivot relative to each other in a controlled manner.

The lower leg cuff 14 also has a plurality of slots 40 and holes 42 formed on opposing extensions 36 to connect and permit adjustability of the lower leg straps 20 with respect to the lower leg cuff 14. A separate set of hinge holes 44 and 46 at the terminal ends of each of the extensions 24 and 36, respectively, of each leg cuff 12 and 14, adjacent to the teeth 26 and 38 also form part of the hinges 16 used to dynamically link the upper leg cuff 12 to the lower leg cuff 14.

In one aspect of the invention, the center segments 22 and 34 of each cuff 12 and 14 have a reduced stiffness as compared to the stiffness of the extensions 24 and 36. In the presently preferred embodiment, this is accomplished by providing each center segment 22 and 34 with a reduced thickness as compared to the thickness of the extensions 24 and 36. This reduction in thickness provides a corresponding reduction in the stiffness of the center segments 22 and 34. For purposes of simplicity and clarity, and since the principles of constructing the upper leg cuff 12 and the lower leg cuff 14 are substantially the same, only the upper leg cuff 12 will be further described herein, except where indicated otherwise.

In accordance with the invention, the reduced thickness of the center segment 22 renders it more bendable than the extensions 24. It also makes the cuff 12 lighter in weight. If desired, a plurality of apertures 48 also may be provided in the center segment 22 to further reduce the weight of the cuff 12 and increase the bendability of the center segment.

Figure 4:
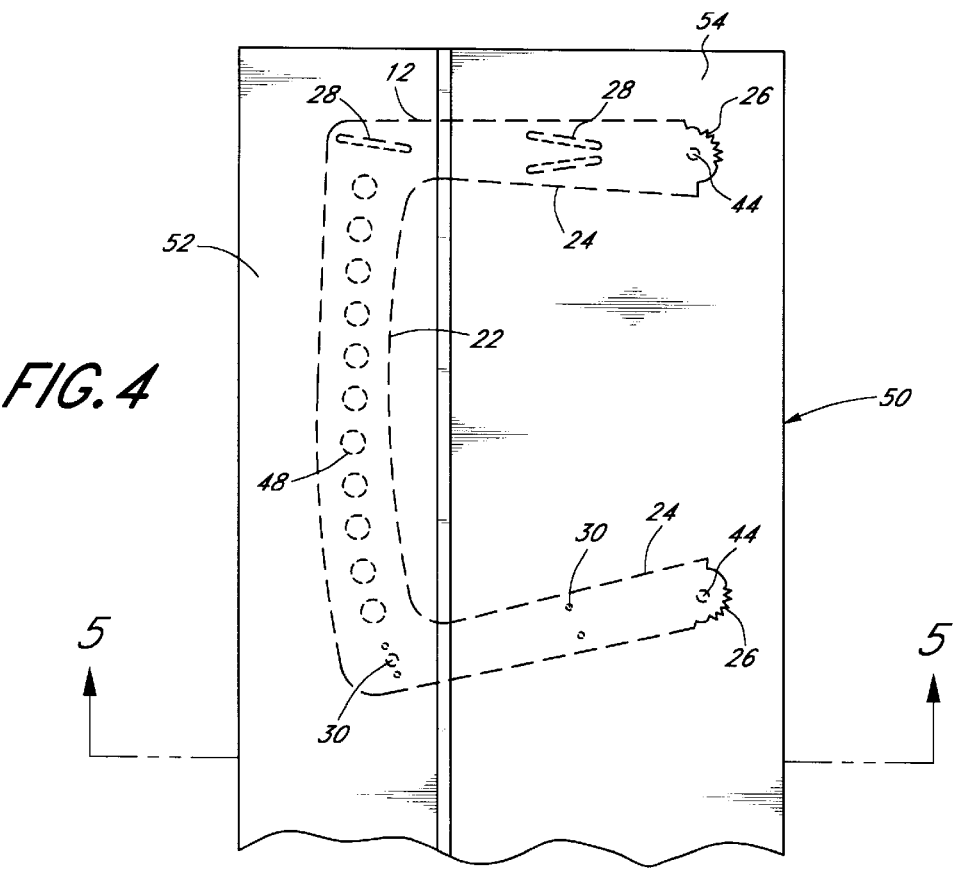
FIG. 4 is a top plan view showing a cuff being formed from a sheet of material having a variable thickness.
Figure 5:
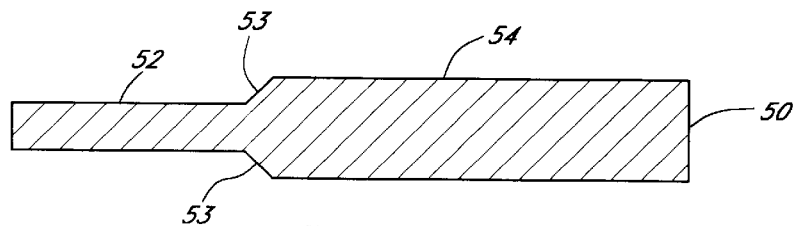
FIG. 5 is a cross-section elevational view taken substantially along the line 5—5 of FIG. 4.

FIGS. 4–5 illustrate one preferred process for fabricating the cuff 12. In the first step of the fabrication process, a substantially planar sheet 50 of material is provided for forming the cuff 12. The sheet 50 preferably is made from metal, such as aluminum, or a composite material, or other suitable material that is rigid, yet capable of being bent to conform to the shape of the wearer's leg.

In one embodiment, the sheet 10 may be formed by an extrusion process. During the extrusion process, a longitudinal portion 52 of the sheet 50 along one edge has a reduced thickness as compared to the remaining portion 54 of the sheet. A tapered transition 53 is provided between the two portions 52 and 54 to prevent stress concentrations. Then, using appropriate stamping techniques, the U-shaped frame comprising the cuff 12 is stamped from the sheet 50. Alternatively, the sheet 50 may be initially formed at a constant thickness, and the longitudinal portion 52 may be machined to reduce its thickness.

For purposes of illustration, FIG. 4 shows the frame of an upper leg cuff 12 (in phantom lines) in a position that would be occupied by the frame relative to the sheet 50 during stamping. Hence, the center segment 22 of the cuff 12 is stamped from a position that overlies the longitudinal portion 52 of the sheet 50 having the reduced thickness, while the extensions 24 of the cuff 12 are stamped from the portion of the sheet 50 that overlies the remaining, thicker portion 54. If desired, as part of the stamping process, the apertures 48 may be stamped in the center segment 22. Alternatively, these apertures 48 may be formed in a separate step, along with the other holes 30 and 44 and slots 28 and in the cuff 12, after the stamping process has been completed.

Figure 6:
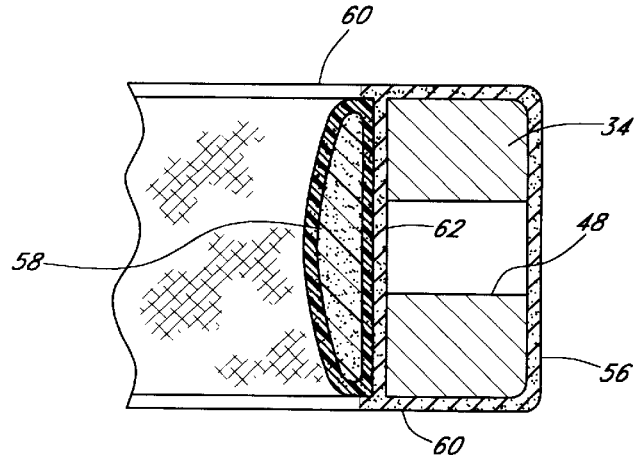
FIG. 6 is a cross-sectional elevational view of a center segment of the cuff, showing the cuff coated by a rubber-like covering and including a pad designed to confront the wearer's leg.

In another aspect of the invention, after the frame has been stamped from the process described above, a molded one-piece resilient covering 56 is applied to selected portions of the frame so that no metal portions of the leg cuffs 12 and 14 are undesirably exposed. In this regard, FIG. 6 shows a cross-section of the lower leg cuff 14 with the covering 56 in place. To apply the covering 56, the cuff 14 is placed in the cavity of a mold, and a rubber-like material is introduced into the cavity to surround selected surfaces of the cuff. The rubber-like material preferably comprises a thermoplastic material that enters the cavity at a relatively high temperature in liquid form, after which it may quickly harden. The rubber-like material forms a resilient protective covering 56 around the cuff 14 that closely and securely engages its surfaces such that it cannot be removed without destroying it. Presently contemplated covering materials include thermoplastic elastomers, such as Krayton resins available from Dynaflex. In one preferred embodiment, two Dynaflex brand resins are blended in ratios of 75% of one resin (No. G-7410-1000-00) and 25% of another resin (No. G-2706-1000-00) to produce a covering 56 that has the appropriate resiliency and processing characteristics.

In addition, a primer may be applied to the cuff 14 prior to being coated with the covering 56. This primer helps the covering 56 adhere better to the cuff 14. One suitable primer includes an elastomeric adhesive available from Chemlok under Nos. EP6962-50A and EP6962-50B.

After the cuff 14 has been coated with the rubber-like covering 56, it is removed from the mold for further processing. This processing includes bending the frame in an arcuate manner such that it is anatomically conformed into a cuff 14 matching the shape of a wearer's leg.

With further reference to FIG. 6, if desired, a pad or cushion 58 may be secured to the center segment 34 of the cuff 14 in confronting relation to the wearer's leg. To facilitate alignment of the pad 58 with respect to the center segment 34, a raised lip 60 may be provided around the pad. In the preferred embodiment, the lip 60 is formed from the rubber-like material defining the covering 56 on the center segment 34. By way of example, as shown in FIG. 6, the raised lip 60 is formed at the outer edges of the center segment 34 and has a continuous perimeter that substantially matches and engages the perimeter of the pad 58. The pad 58 may be secured to the center segment 34 by a strip of Velcro material 62. This Velcro material 62 may be received within a recess defined by the covering 56 in the area where the pad 58 is secured to the center segment.

From the foregoing, it will be appreciated that the present invention provides an orthopaedic brace cuff 12 or 14 that can be quickly and conveniently fabricated at a relatively low cost. Since the cuff 12 or 14 is formed as a single piece and then coated in a single step with the rubber-like covering 56, a very strong and light-weight cuff is produced with a minimum number of manufacturing steps, thereby keeping the cost as low as possible. Since there are no overlapping joints connected by rivets or other fasteners that could tend to weaken or otherwise loosen during use, the cuff 12 or 14 has a relatively high degree of strength. The absence of joints and rivets further contributes to a cuff having a highly streamlined and desirable cosmetic appearance. Further, the overall weight of the cuff is as low as possible, due to the reduced thickness in the area of the center segment and the apertures 48 which make it more readily bendable during the fabrication process.

While a particular form of the invention has been illustrated and described, it will be apparent that various modifications can be made without departing from the spirit and scope of the invention. Therefore, it is not intended that the invention be limited, except as by the appended claims.

What is claimed is:

1. In an orthopaedic brace for bridging and stabilizing a human body joint, said brace having two hinges respectively on opposite sides of said joint, a cuff comprising:

a generally U-shaped frame formed of a single piece of bendable sheet material, shaped to conform to the body part of a wearer, said frame having a center segment and two substantially parallel extensions projecting from the ends of said center segment, each of said extensions being configured to project toward said joint when said frame is properly positioned during use and terminating at an end distal to said center segment by means cooperating with a respective one of said hinges; and a molded one-piece hardened protective covering that closely and securely engages opposite surfaces of said center segment and said extensions such that it cannot be removed from said frame without destroying it.

2. The cuff of claim 1, wherein said center segment has a reduced stiffness as compared to said extensions to facilitate bending of said center segment to fit a particular wearer.

3. The cuff of claim 1, wherein said frame is formed of aluminum.

4. The cuff of claim 1, wherein said cuff is formed of a composite material.

5. The cuff of claim 1, wherein said center segment is of reduced thickness as compared to said extensions.

6. The cuff of claim 1, wherein:

said frame is aluminum; and said center segment is of reduced thickness compared to said extensions.

7. The cuff of claim 6, wherein said center segment defines a series of apertures, thereby rendering the center segment lighter and more readily bendable.

8. The cuff of claim 1, wherein said covering defines a recess for receiving a pad extending at least across a portion of said center segment.

9. The cuff of claim 8, wherein said covering defines a raised lip surrounding said recess.

10. The cuff of claim 1, wherein said covering is made of a thermoplastic material.

11. A frame for an orthopaedic brace for bridging and stabilizing a human body joint, said brace having two hinges respectively on opposite sides of said joint, comprising a generally U-shaped single piece of bendable sheet material shaped to conform to the body part of a wearer adjacent said joint, said frame having a center segment and two substantially parallel extensions projecting from the ends of said center segment, each of said extensions being configured to project toward said joint when said frame is properly positioned during use and terminating at an end distal to said center segment by means cooperating with a respective one of said hinges, at least a portion of said center segment being of reduced thickness as compared to said extensions to facilitate bending of said center segment to fit a particular wearer.

12. The frame of claim 11 further comprising said frame being composed of aluminum or of a composite material.

13. The frame of claim 12 further comprising said frame being composed of aluminum.

14. The frame of claim 12 further comprising said frame being composed of a composite material.

15. The frame of claim 11 wherein said thickness is reduced by an amount sufficient to receive a pad in the recess formed by said reduction in thickness.

16. The frame of claim 11 wherein said center segment contains at least one aperture rendering said center segment lighter and more readily bendable.

17. The frame of claim 16 wherein there are a plurality of apertures in said center segment.

* * * * *